United States Patent
Ye et al.

(10) Patent No.: US 7,362,500 B2
(45) Date of Patent: Apr. 22, 2008

(54) DOUBLE-CLAD FIBER SCANNING MICROSCOPE

(75) Inventors: Jing Yong Ye, Ann Arbor, MI (US); Theodore B. Norris, Dexter, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 4 days.

(21) Appl. No.: 10/556,620

(22) PCT Filed: May 28, 2004

(86) PCT No.: PCT/US2004/016829

§ 371 (c)(1),
(2), (4) Date: Nov. 15, 2005

(87) PCT Pub. No.: WO2004/106985

PCT Pub. Date: Dec. 9, 2004

(65) Prior Publication Data

US 2007/0002435 A1    Jan. 4, 2007

Related U.S. Application Data

(60) Provisional application No. 60/474,113, filed on May 29, 2003.

(51) Int. Cl.
*G02B 21/00* (2006.01)
*G02B 21/06* (2006.01)

(52) U.S. Cl. .................. 359/368; 359/385; 359/391
(58) Field of Classification Search ........ 359/368–390; 385/123–128, 33
See application file for complete search history.

(56) References Cited

U.S. PATENT DOCUMENTS

| | | | | |
|---|---|---|---|---|
| 4,330,169 A * | 5/1982 | Kantor | .................. | 359/369 |
| 4,500,204 A * | 2/1985 | Ogura | .................. | 356/318 |
| 5,168,157 A | 12/1992 | Kimura | | |
| 5,323,009 A * | 6/1994 | Harris | .................. | 250/458.1 |
| 5,389,779 A * | 2/1995 | Betzig et al. | .................. | 250/216 |
| 5,452,382 A | 9/1995 | Shionoya et al. | | |
| 5,742,429 A * | 4/1998 | Tsumanuma et al. | ....... | 359/377 |
| 5,822,488 A * | 10/1998 | Terasawa et al. | ........... | 385/127 |
| 6,160,568 A * | 12/2000 | Brodsky et al. | ............ | 347/247 |
| 6,236,783 B1 * | 5/2001 | Mononobe et al. | ........... | 385/43 |
| 6,411,835 B1 | 6/2002 | Modell et al. | | |
| 6,485,413 B1 | 11/2002 | Boppart et al. | | |
| 6,757,467 B1 * | 6/2004 | Rogers | .................. | 385/126 |
| 7,046,888 B2 * | 5/2006 | Ye et al. | .................. | 385/126 |

FOREIGN PATENT DOCUMENTS

EP    1207387 A1    5/2002

* cited by examiner

*Primary Examiner*—Thong Q Nguyen
(74) *Attorney, Agent, or Firm*—Harness, Dickey & Pierce, P.L.C.

(57) ABSTRACT

A scanning microscope having a laser outputting an excitation laser beam and a fiber member having a first core and a second core. The second core is generally disposed within the first core and is operable to receive the excitation laser beam from the laser and transmit the excitation laser beam to a sample to be tested. A moveable stage supports an end of the fiber member and/or a sample to be tested and is operable to move the end of the fiber member and the sample to be tested relative to each other.

17 Claims, 3 Drawing Sheets

DOUBLE-CLAD FIBER SCANNING MICROSCOPE

CROSS-REFERENCE TO RELATED APPLICATIONS

This application claims the benefit of U.S. Provisional Application No. 60/474,113, filed on May 29, 2003. The disclosure of the above application is incorporated herein by reference.

GOVERNMENT RIGHTS

This invention was made with government support under Contract No. N01-CO-27173 awarded by the National Cancer Institute, National Institutes of Health. The Government has certain rights in the invention.

FIELD OF THE INVENTION

The present invention relates to scanning microscopes and, more particularly, to a scanning microscope using a double-clad fiber for improved detection efficiency.

BACKGROUND AND SUMMARY OF THE INVENTION

Confocal microscopy was first invented by Marvin Minsky in 1957. Initially, stage scanning was employed to obtain an image by moving a specimen in a raster pattern across a focused point of a stationary light beam. An exit pinhole is placed in the image plane conjugated to the spot being scanned so that only the signal originating from the focused spot is transmitted through the pinhole, while out-of-focus signals are prevented from reaching a detection system. A confocal microscope therefore generally has a higher resolution than a wide-field microscope, and more importantly, it has sectioning capability to achieve a 3-D image. The benefit of stage scanning is that the field of view is vastly expanded, because the area that can be imaged is determined by the travel range of the scanning stage rather than the optics in the microscope. However, there are drawbacks that limit its application. The scanning rate is extremely slow because it requires time to translate the massive stage precisely. In addition, a moving stage causes vibration problems to samples, especially liquid-bathed biological samples. These problems were circumvented when laser scanning confocal microscope was developed into a practical instrument in the late 1980s, where beam scanning was controlled by two galvanometer mirrors that are imaged onto the entrance pupil of an objective lens. Thus, only the direction of the incident excitation light rays is deviated at the entrance plane, while the pupil remains fully illuminated throughout the scanning. Accordingly, the focus spot of the laser beam out of the objective scans across the sample to be imaged. The beam scanning with the galvanometer mirrors has much higher scanning rates, and samples are not disturbed by vibrations, because there is no movement of sample stage. However, the beam scanning also has its own shortcomings. Because the incident angle of the laser beam on the entrance pupil of an objective lens has to vary in a certain range, associated aberrations are inevitable even with an expensive high quality objective lens. In addition, the field of view is severely limited by the acceptable angle of the objective. Although the invention of multiphoton confocal microscopes enhanced the detection efficiency by omitting the exit pinholes, the basic scanning mechanism remains the same as previous confocal microscopes.

As briefly mentioned above, both stage- and beam-scanning confocal microscopes have their own disadvantages, despite the fact that they are indispensable tools in many research fields, especially in biological studies. In the present invention, a novel double-clad fiber based scanning confocal microscope, which possesses the advantages of both stage- and beam-scanning configurations, while overcomes all the main disadvantages of conventional confocal microscopes. In addition, the present invention further provides important new features, such as increased flexibility and low cost.

According to the principles of the present invention, a scanning microscope having a laser outputting laser energy is provided. A fiber member having a first core and a second core is coupled to the laser. The second core of the fiber member is generally disposed within the first core, which also acts as the first cladding for the second core. The second core is sized smaller than the first core. The first core is surrounded by a second cladding. An opposing end of the fiber member is mounted to a moveable stage for movement therewith.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENT

The following description of the preferred embodiment is merely exemplary in nature and is in no way intended to limit the invention, its application, or uses.

In contrast to conventional beam scanning, which includes changing the angle of an incident beam at an objective lens, the beam scanning of the present invention can be achieved by moving an optical fiber, which delivers a laser beam for excitation and collects signals back along the same fiber. Conventional fibers, either single-mode or multimode fibers, cannot be practically used in this way. Although a single-mode fiber (SMF) has an acceptable mode for excitation, the numerical aperture (NA) is typically only about 0.1, which results in a very inefficient signal collection. On the other hand, although a multimode fiber multimode fiber has a larger numerical aperture that is good for collecting signals, the output mode is unable to be tightly focused, thus resulting in inefficient excitation and low resolution. In addition, in case of multiphoton excitation, the multimode fiber leads to further lower excitation rate, because an ultra short laser pulse is severely deformed during propagating through a multimode fiber.

Figure 1:
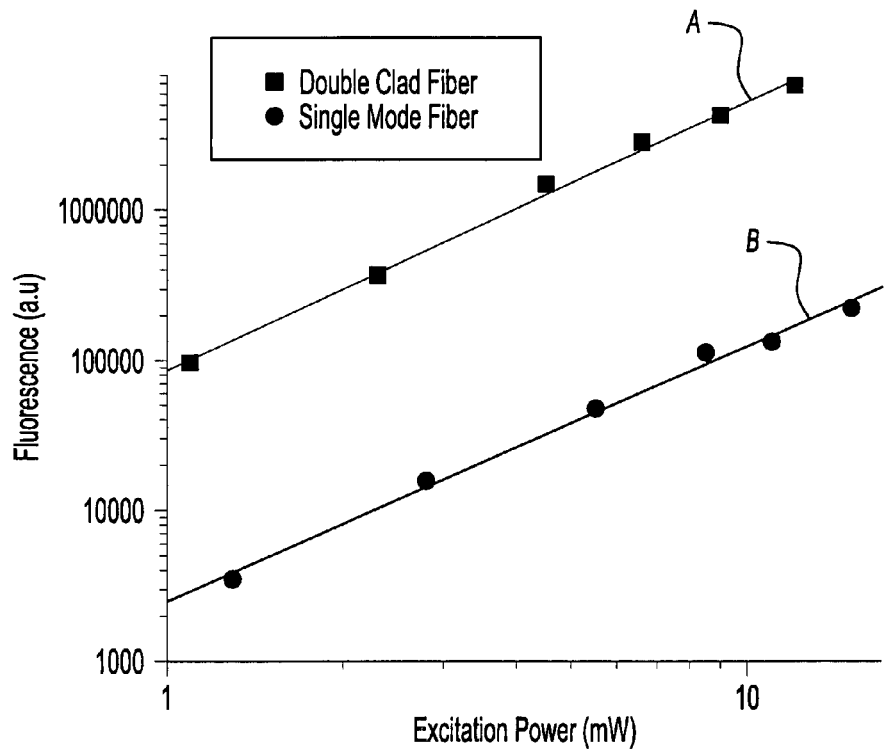
FIG. 1 is a graph illustrating that the detected two-photon fluorescence power through a double-clad fiber in comparison with a single-mode fiber.

In order to address this trade-off issue for biosensing, a double-clad fiber may be used for enhancing both excitation and collection efficiency for through-fiber biosensing as described in U.S. Provisional Application No. 60/434,604. This application is incorporated herein by reference. In that application, two-photon fluorescence detection sensitivity, represented by line A, is increased by a factor of 40 using a photonic crystal double-clad fiber in comparison with a conventional SMF, represented by line B (see FIG. 1).

Figure 2:
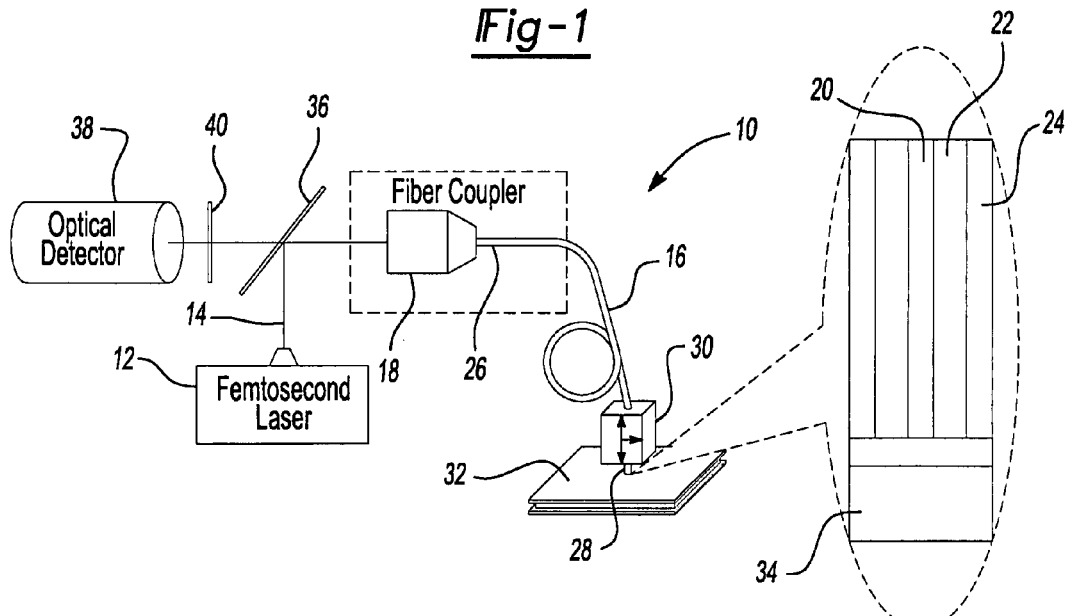
FIG. 2 is a schematic view illustrating a double-clad fiber scanning microscope of the present invention.

Referring to FIG. 2, a schematic diagram of a double-clad fiber scanning microscope, generally indicated at 10, is illustrated, although it should be understood that alternative configurations might also be possible based on this double-clad fiber scanning mechanism. Double-clad fiber scanning microscope 10 is illustrated having a laser 12 capable of outputting a laser beam 14, which will also be referenced as excitation laser beam. Laser 12 is operably coupled to a double-clad fiber or fiber member 16 via a fiber coupler 18. More specifically, double-clad fiber 16 includes an inner core 20, an outer core 22, and an outer cladding 24. Inner core 20 is illustrated being coaxial with each of outer core 22 and outer cladding 24; however, it should be understood that this is not required. It should be noted that outer core 22 also serves as an inner cladding to inner core 20 and, thus, serves a dual purpose. It should be understood that double-clad fiber 16 may be a fiber member system comprised of a plurality of fibers 16.

Laser 12 is coupled with double-clad fiber 16 through fiber coupler 18 such that laser beam 14 is introduced into inner core 20 at a proximal end 26 of double-clad fiber 16. A distal end 28 of double-clad fiber 16 is coupled to a 3-D rapid scanning stage 30 that is operable to move laser beam 14, exiting distal end 28 of double-clad fiber 16, across a sample of interest 32. A micro-lens 34, such as a GRIN lens, may be attached to distal end 28 of double-clad fiber 16 to focus laser beam 14 to an even smaller spot to achieve higher resolution. Resultant signals, such as, but not limited to, flourescence signals, Raman signals, back reflection of the laser beam 14, and the like), emitted from sample of interest 32 are then collected back through both inner core 20 and outer core 22 of double-clad fiber 16 and separated from excitation laser beam 14 using an optical separation system 36, such as a dichroic mirror, before reaching an optical detection system 38. A filter 40 may also be used for filtering undesirable signals from reaching optical detection system 38.

With respect to double-clad fiber 16, the numerical apertures of the inner core and outer core (inner clad) can be adjusted independently. The outer core numerical aperture can be as large as about 0.8 or even just in air, which is comparable with most high magnification objective lenses. Furthermore, when a lens, such as a gradient index (GRIN) lens, is connected with double-clad fiber 16 to further focus excitation light, the collection efficiency of fluorescence signals received back from the lens to the double-clad fiber is high, because the larger outer core can efficiently collect fluorescence even if chromatic aberration of the lens exists. The resultant signal collection efficiency is low if a conventional fiber is used in this case.

Figure 3A:
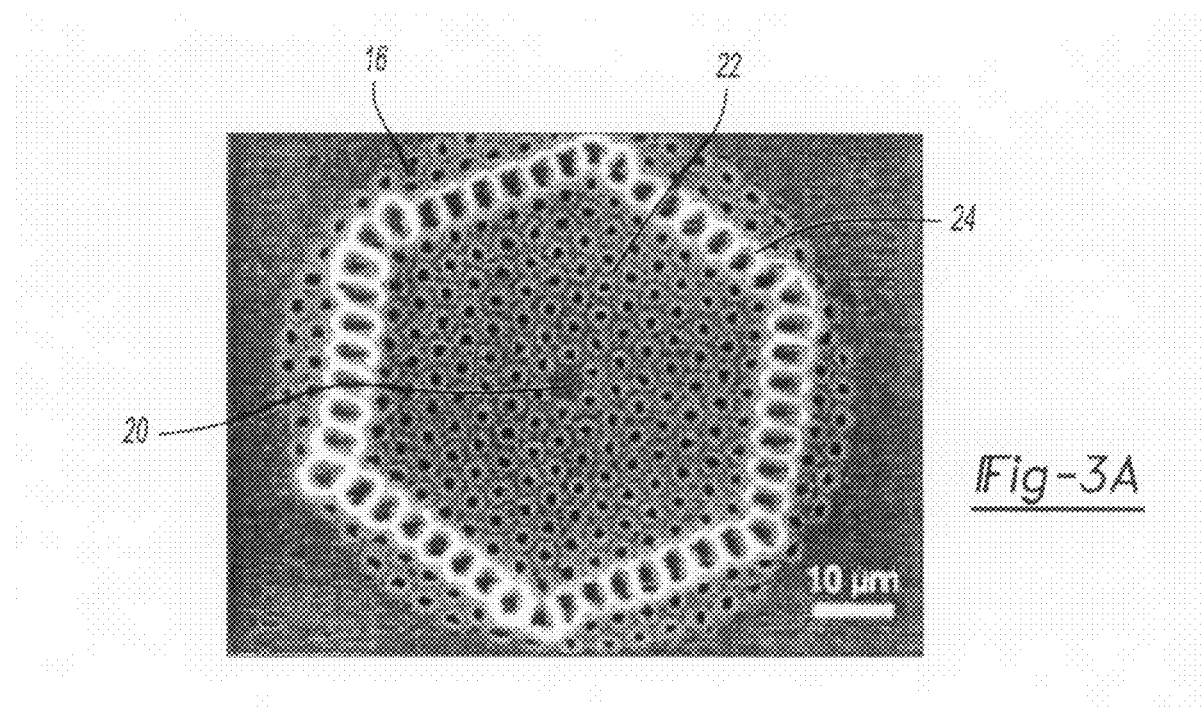
FIG. 3A is an end view of the distal end of a double-clad fiber.
Figure 3B:
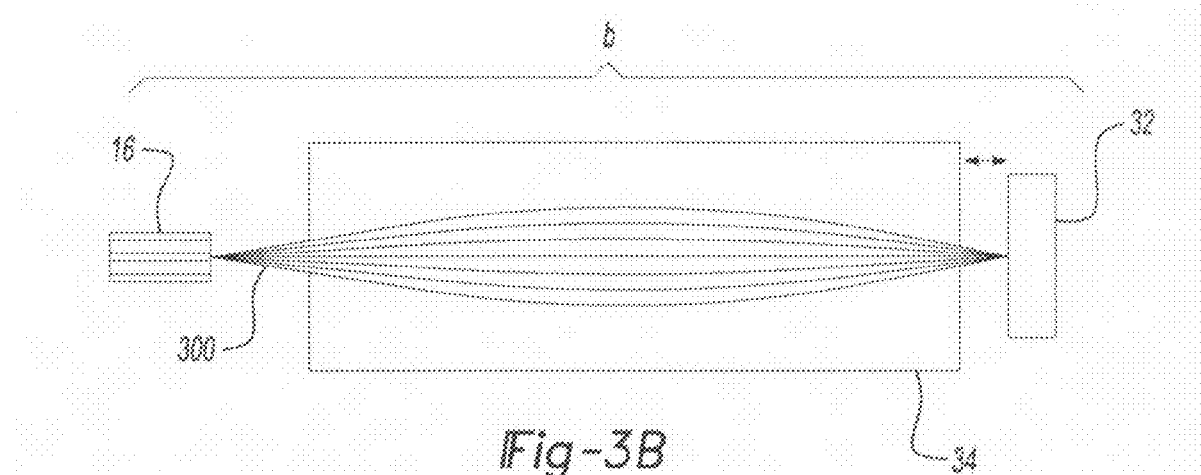
FIG. 3B is a schematic illustration of a GRIN lens coupled to the excitation beam output from the fiber and focusing the excitation beam into a sample.
Figure 3C:
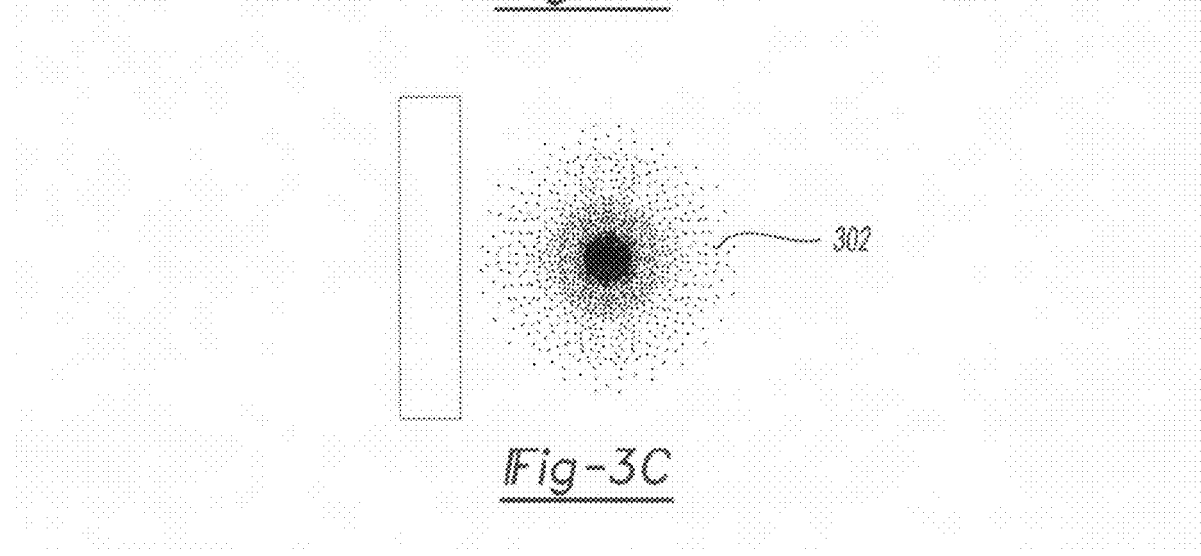
FIG. 3C is a schematic representation of the area of the resultant signal at the focal plane of the excitation beam in the sample of FIG. 3B.
Figure 3D:
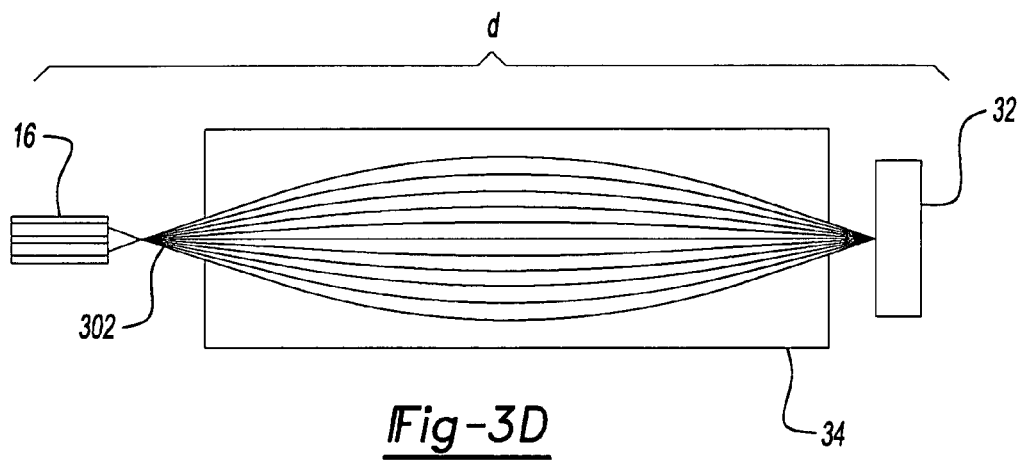
FIG. 3D is a schematic representation of a GRIN lens used to collect the resultant signal from the sample back to the end of the fiber.
Figure 3E:
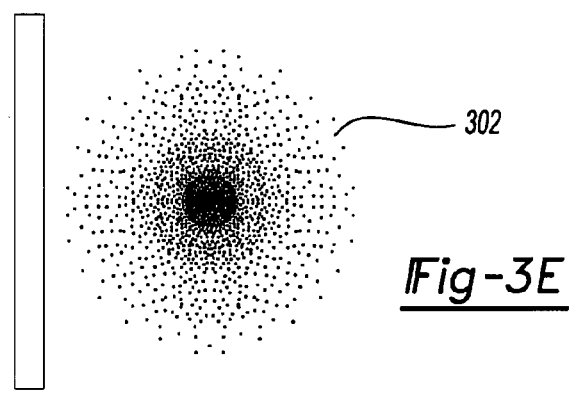
FIG. 3E is a schematic representation of the footprint of the resultant signal of FIG. 3D that is formed on the end of the fiber due to aberrations and/or other anomalies.

FIGS. 3A-3E illustrate that the collected fluorescence from a GRIN lens forms a large spot on distal end 28 of double-clad fiber 16. That is, as seen in FIG. 3A, distal end 28 of double-clad fiber 16 includes the aforementioned inner core 20 and outer core 22. As seen in FIG. 3B, when an excitation beam 300 exits double-clad fiber 16 it passes through a lens 34, such as a GRIN lens, and is focused on sample 32. The excitation beam 300 causes a resultant signal 302 to be produced from sample 32 generally indicated in FIG. 3C. This resultant signal 302 may, for example, have a radius of about 1 µm. However, as seen in FIG. 3D, resultant signal 302 then passes back through lens 34. Ideally, resultant signal 302 would be focused perfectly on distal end 28 of double-clad fiber 16. However, due to chromatic aberration and/or other anomalies, a larger footprint of resultant signal 302 is produced and may have a radius of about 49 µm, as seen in FIG. 3E. In conventional collection, this larger footprint would not be collected and thus would reduce the efficiency of the system. However, in the present invention, outer core 22, having a high numerical aperture, is capable of collecting more of resultant signal 302, thereby providing improved detection efficiency.

As should be appreciated, double-clad fiber scanning microscope 10 of the present invention provides a number of advantages over conventional scanning microscopes. For example, as described above, double-clad fiber scanning microscope 10 has extremely simple structure.

However, it has revolutionary and fundamental changes of the scanning mechanism, which ensures many unique features of this new type of scanning microscope.

Excellent Flexibility

Double-clad fiber scanning microscope 10 of the present invention is extremely flexible. More particularly, double-clad fiber scanning microscope 10 can be freely adjusted without affecting the excitation source and the detection, because the scanning head containing distal end 28 of double-clad fiber 16 is controlled by small translation (i.e. x-y or x-y-z) of scanning stage 30 through a single fiber. Thus, scan, imaging can be performed in either upright or inverted configurations, or at an arbitrary angle, if needed. Scanning stage 30 can also easily achieve any scanning pattern on a sample of interest. Still further, scanning stage 30 can be used to construct a stand-alone microscope together with an excitation source and detection system. It can also be used as a unit to be incorporated into a conventional light microscope. For instance, scanning stage 30 can be made as a standard component to be screwed in a nosepiece. Thus, one can easily convert a conventional microscope into a scanning microscope with the beneficial functions as described herein.

Large Scanning Range

Unlike conventional beam scanning microscope, the scanning range of double-clad fiber scanning microscope 10 is determined by the travel range of scanning stage 30 used to control distal end 28 of double-clad fiber 16. In fact, it has been found that this travel range may be increased to millimeters or larger while maintaining high resolution, such as less than a micron. This feature allows one to obtain a whole image of a large sample. For example, a conventional beam-scanning microscope has a scanning range only on a cellular scale due to the limited field of view of the objective lens. In contrast, the new beam-scanning mechanism based on double-clad fiber 16 makes it possible to image a whole organism or a tumor with a single scan.

Fast Scanning

Fast scan rate is required for constructing a practical instrument. For conventional stage-scanning microscope, the scan rate is normally very slow, because it takes time to translate a massive stage together with a sample and sample holder. The scanning mechanism described herein only involves moving a lightweight fiber tip. Similar to scanner mirrors used in beam scanning, the fiber tip can scan in a fast rate with a rapid scanner.

No Vibrations to the Sample

Despite the fast scan rate noted above, there is no vibration disturbing the imaging sample, because the sample remains stationary during the scanning process, which is in contrast to stage scanning. Beside the light weight of the fiber tip, this is another practical reason that fast scan rate is allowed here. In addition, far field excitation from a fiber tip is utilized here to achieve a quiet beam scan, which avoids an inevitable problem in near field scanning optical microscopy where interaction between a scanning tip and samples is generally a serious problem.

Aberration-free Scanning

In conventional beam scanning, two scanner mirrors are used to change the incident angle of excitation light at the entrance pupil of an objective lens, which causes severe off-axis aberrations. It is very difficult and costly to design and fabricate an objective lens that is corrected for the off-axis aberrations. Moreover, even with a lot of effort, one still must compromise between the field of view and the image quality, because the off-axis aberration is hard to be fully compensated, especially for a relatively large fields of view. The scanning of excitation beam with flexible double-clad fiber 16 fundamentally solved the problem of aberrations associated with conventional beam scanning. In double-clad fiber scanning microscope 10, each scanned point of a sample is equally illuminated and signal collection remains the same throughout the entire scanning range. This feature ensures a high quality image of a large sample of interest.

Low Cost

The cost for constructing double-clad fiber scanning microscope 10 is much lower than a conventional beam-scanning microscope with a scan unit based on- scanner mirrors. As described above, the requirement of an objective lens is important in order to achieve a relatively large flat field of view and to compensate for off-axis aberrations. In addition, an imaging system with high optical quality is also needed to image the scanner mirrors onto the entrance pupil of the objective lens. These factors make a conventional beam-scanning microscope very expensive.

In contrast, in double-clad fiber scanning microscope 10, the objective lens used in fiber coupler 18 solely focuses light onto proximal end 26 of double-clad fiber 16. Thus, the objective lens in fiber coupler 18 satisfies the requirements, yet may be manufactured relatively inexpensively. The beam scanning is achieved by controlling distal end 28 of fiber double-clad fiber 16 with a scanning stage 30, which replaces the expensive scanning unit composed of scanner mirrors and a high quality imaging system used in conventional beam-scanning microscope. Therefore, the new scanning mechanism based on double-clad fiber 16 makes it possible to construct a low cost, high performance microscope.

C. Double-clad Fiber Array Scanning Microscope

Figure 4:
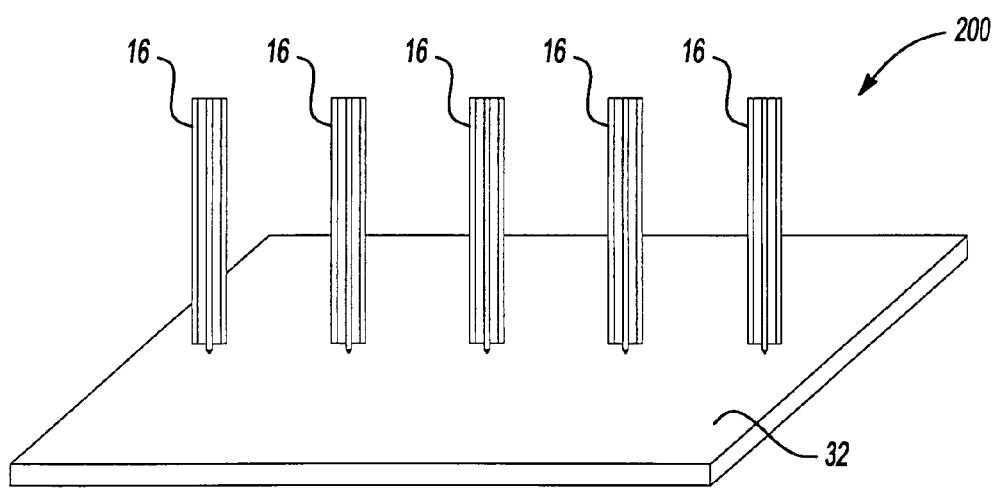
FIG. 4 is a perspective view of a double-clad fiber array used as a scanning head.

In the above, a double-clad fiber scanning microscope 10 utilizing a single double-clad fiber 16 is discussed. However, it has been determined that the scanning rate can be further enhanced by using a 1-D or 2-D array, generally indicated at 200, of double-clad fibers 16, as illustrated in FIG. 4.

Excitation light can be coupled into double-clad fiber array 200 utilizing existing techniques, such as a MEMS switch. When double-clad fiber array 200 scans simultaneously instead of scanning a single fiber, the scan rate increases by a factor of the number of double-clad fibers in the array. For example, employing five double-clad fibers 16 aligned with 1 mm spacing between each other and mounted on a single translation stage 30, a 5-mm line to be scanned only requires a translation of 1 mm. Thus, the scan rate increases by five times compared with a single fiber scanning. If a 2-D array of double-clad fibers is used, one should be able to maintain a high scan rate even for a large imaging area.

A novel mechanism for a new generation of scanning microscopes based on double-clad fiber scanning is provided. This microscope overcomes the drawbacks of conventional stage- and beam-scanning microscopes, and possesses many advantages as described above, i.e., excellent flexibility, large scanning range, fast scan rate, quiet scanning, aberration-free scanning, and low cost. With all these benefits integrated into one microscope, a wide range of potential applications is anticipated.

The description of the invention is merely exemplary in nature and, thus, variations that do not depart from the gist of the invention are intended to be within the scope of the invention. For example, scanning stage 30 can support the sample of interest 32 and be used to move the sample of interest 32 relative to distal end 28 of double-clad fiber 16. Such variations are not to be regarded as a departure from the spirit and scope of the invention.

What is claimed is:

1. A scanning microscope comprising:
   a laser outputting an excitation laser beam;
   a fiber member having a first core and a second core, said second core being generally disposed within said first core, said second core being operable to receive said excitation laser beam from said laser and transmit said excitation laser beam to a sample to be tested;
   a lens operably coupled to an end of said fiber member through which said excitation laser beam exits, said lens operable to achieve increased resolution and increased excitation of said sample to be tested, said lens moving with movement of said end of said fiber member; and
   a moveable stage supporting at least one of a group consisting of said end of said fiber member and said sample to be tested, said moveable stage being operable to move said end of said fiber member and said sample to be tested relative to each other, wherein said excitation laser beam impacts said sample to be tested to produce a resultant signal representative of said sample to be tested, and said first core being operable to collect said resultant signal from said sample to be tested independently of said second core collecting said resultant signal.

2. The scanning microscope according to claim 1 wherein said resultant signal is a flourescence signal.

3. The scanning microscope according to claim 1 wherein said resultant signal is a Raman signal.

4. The scanning microscope according to claim 1 wherein said resultant signal is a back reflection signal of said excitation laser beam.

5. The scanning microscope according to claim 1, further comprising:
- an optical separation system operably coupled to receive both said excitation laser beam and said resultant signal; and
- an optical detection system operably coupled to said optical separation system,
- wherein said optical separation system permits transmission of said resultant signal to said optical detection system.

6. A scanning microscope comprising:
- a laser source outputting an excitation laser beam;
- a fiber member system having a plurality of fiber members, each of said plurality of fiber members having a first core and a second core, the second core being generally disposed within the first core, said second core being operable to receive said excitation laser beam from said laser source and transmit said excitation laser beam to a sample to be tested to generate a resultant signal from said sample;
- an optical separation system operably coupled to receive both said excitation laser beam and said resultant signal; and
- an optical detection system operably coupled to said optical separation system,
- wherein said first cores of each of said plurality of fiber members is operable to collect said resultant signal from said sample to be tested independently of an associated second core collecting said resultant signal and said optical separation system permits transmission of said resultant signal to said optical detection system for detection.

7. The scanning microscope according to claim 6, further comprising:
- a moveable stage supporting at least one of a group consisting of said fiber member system and said sample to be tested, said moveable stage being operable to move said fiber member system and said sample to be tested relative to each other.

8. The scanning microscope according to claim 6 wherein said resultant signal is a flourescence signal.

9. The scanning microscope according to claim 6 wherein said resultant signal is a Raman signal.

10. The scanning microscope according to claim 6 wherein said resultant signal is a back reflection signal of said excitation laser beam.

11. The scanning microscope according to claim 6 wherein each of said second cores is co-axial with an associated one of said first cores.

12. The scanning microscope according to claim 6, further comprising:
- a fiber coupler coupled to said fiber member system for transmitting said excitation laser beam and said resultant signal therethrough.

13. The scanning microscope according to claim 6 wherein said sample is biological tissue.

14. The scanning microscope according to claim 6, further comprising:
- a lens operably coupled to said fiber member system, said lens operable to achieve improved resolution and increased excitation of said sample.

15. The scanning microscope according to claim 14 wherein said lens is a Gradient Index lens.

16. A scanning microscope comprising:
- a laser outputting an excitation laser beam;
- at least one fiber member having a first core and a second core, the second core being co-axial within the first core, the second core being operable to receive the excitation laser beam from the laser and transmit the excitation laser beam to a sample to be tested, the first and second cores being independently operable to receive a resultant signal generated by the excitation laser beam contacting the sample to be tested;
- a lens operably coupled to an end of the at least one fiber member through which the excitation laser beam exits, said lens moving with movement of the end of the at least one fiber member; and
- a moveable stage coupled to the end of the at least one fiber member with the coupled lens, the moveable stage being operable to move the end of the at least one fiber member and the coupled lens relative to the sample to be tested.

17. The scanning microscope of claim 16, further comprising:
- an optical separation system operably coupled to receive both said excitation laser beam and said resultant signal; and
- an optical detection system operably coupled to said optical separation system,
- wherein said optical separation system permits transmission of said resultant signal to said optical detection system for detection.

* * * * *

UNITED STATES PATENT AND TRADEMARK OFFICE
CERTIFICATE OF CORRECTION

PATENT NO. : 7,362,500 B2  Page 1 of 1
APPLICATION NO. : 10/556620
DATED : April 22, 2008
INVENTOR(S) : Ye et al.

It is certified that error appears in the above-identified patent and that said Letters Patent is hereby corrected as shown below:

Column 3, lines 8-9, after "multimode fiber" delete "multi-mode fiber".

Column 3, line 54, after "like" delete ")".

Column 4, line 47, after "scan" delete ",".

Column 6, line 5, delete "C." before "Double-clad".

Signed and Sealed this

Sixteenth Day of September, 2008

JON W. DUDAS
*Director of the United States Patent and Trademark Office*